United States Patent [19]

McGandy

[11] 4,285,792
[45] Aug. 25, 1981

[54] PORTABLE PH METER FOR EFFLUENTS HAVING A SELF-CLEANING ELECTRODE CHAMBER

[75] Inventor: Edward L. McGandy, Shaker Heights, Ohio

[73] Assignee: Standard Oil Company (Ohio), Cleveland, Ohio

[21] Appl. No.: 173,777

[22] Filed: Jul. 30, 1980

[51] Int. Cl.³ ............................................. G01N 27/38
[52] U.S. Cl. ................................. 204/195 R; 324/438
[58] Field of Search .......... 204/195 R, 195 G, 195 F, 204/1 H; 324/438; 422/68

[56] References Cited

U.S. PATENT DOCUMENTS

| | | | |
|---|---|---|---|
| 3,155,603 | 11/1964 | Hart | 204/195 R |
| 3,438,872 | 4/1969 | Johansson | 204/1 T |
| 4,021,199 | 5/1977 | Mukae | 204/195 R X |

FOREIGN PATENT DOCUMENTS

| | | | |
|---|---|---|---|
| 52-12893 | 1/1977 | Japan | 204/195 R |
| 52-17890 | 2/1977 | Japan | 204/195 R |

Primary Examiner—G. L. Kaplan
Attorney, Agent, or Firm—David J. Untener; Herbert D. Knudsen; Larry W. Evans

[57] ABSTRACT

A self-cleaning apparatus (10) for the monitoring of pH in an effluent process stream (17) includes a sump pump (16) for sampling the effluent process stream (17), a housing (12) for supporting a pH electrode (13), and a cleansing assembly (15) for automatically cleansing the pH electrode (13) entirely powered by the impingement of the fluid process stream (17) upon the cleansing assembly (15). The housing (12) includes an electrode chamber (14) into which the pH electrode (13) extends. The electrode chamber (14) receives the effluent process stream (17) sample from the sump pump (16) and is also automatically, continuously cleansed by the cleansing assembly (15).

9 Claims, 3 Drawing Figures

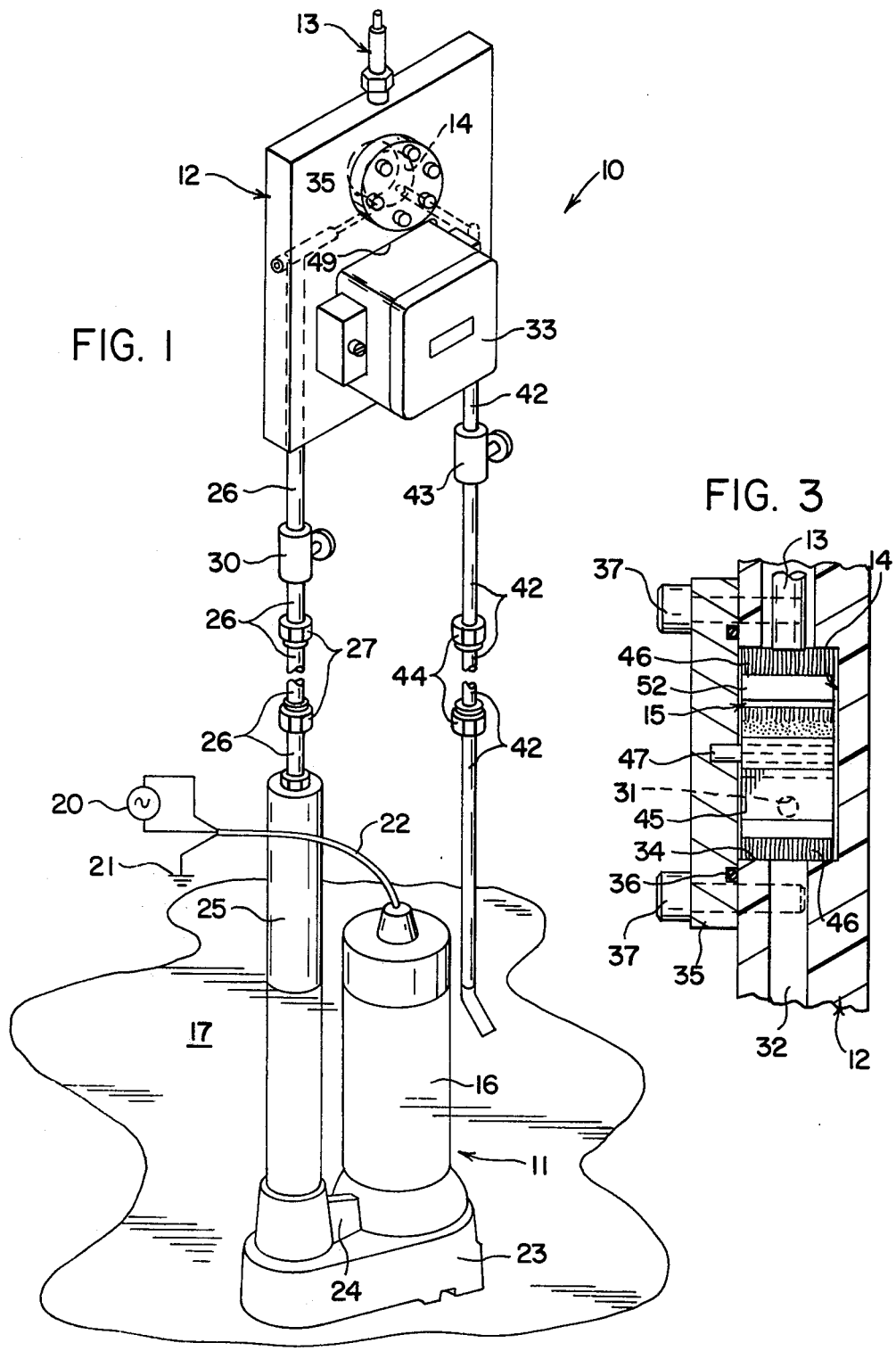

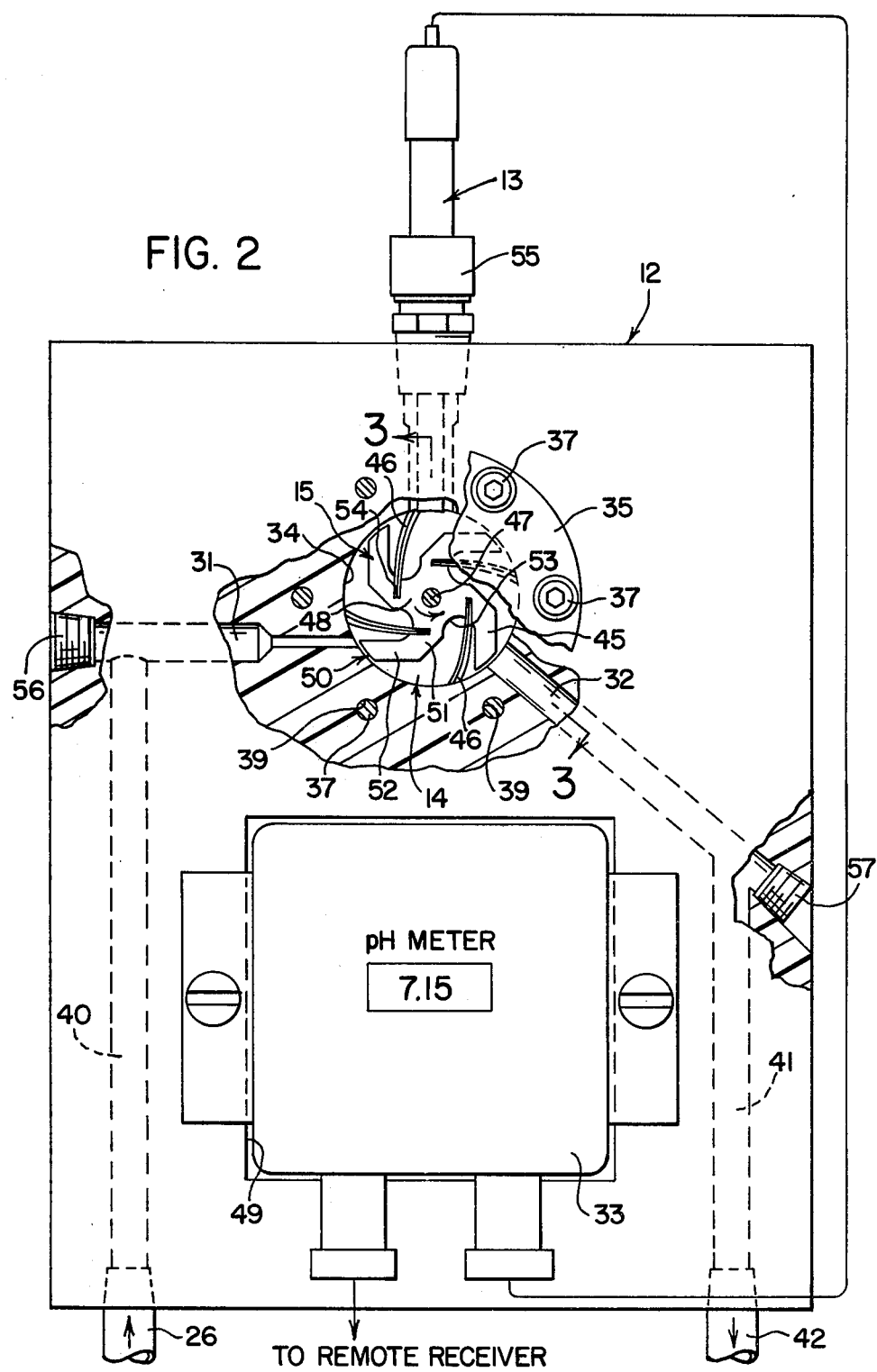

… … … …

PORTABLE PH METER FOR EFFLUENTS HAVING A SELF-CLEANING ELECTRODE CHAMBER

TECHNICAL FIELD

The present invention relates generally to pH monitoring of effluent waste for environmental or treatment purposes. More particularly, the present invention relates to a portable pH metering system wherein the electrode chamber and the electrodes are continually, automatically cleansed to prevent the deleterious build-up of oily wastes and insoluble sediments.

BACKGROUND ART

Proper purification of waste water requires measurement of electrochemical properties such as pH. In many waste water treatment facilities, and especially those of an industrial nature, the incoming aqueous effluent is an admixture of oily wastes and insoluble sediments. Immersed in such effluents, existing pH monitoring equipment are often rendered inoperable, and at the very least require frequent cleansing maintenance.

Efforts to minimize maintenance and downtime have centered about reducing exposure to the effluent such as by diverting a portion of the process fluid to be tested into a separate housing in which the pH electrodes are inserted. However, this procedure has heretofore demanded costly permanent sampling installations at each location where pH is to be monitored. Additionally, the housing and electrodes still have needed frequent maintenance and been subject to failure as a result of oil and sediment build-up in the vicinity of the electrodes. Although several approaches have been taken to clean the electrodes during operation, including oscillating motor-driven wipers, ultrasonic vibrations, and timed jets of cleansing solution aimed at the electrodes, all have required complex and expensive independent structure to effectuate.

DISCLOSURE OF THE INVENTION

It is, therefore, an object of the invention to provide an economical pH metering apparatus for effluents having an electrode chamber that is automatically and continuously cleansed to prevent build-up of oily wastes and insoluble sediments.

It is another object of the invention to provide a pH metering apparatus for effluents, as above, in which a mechanically powered brush arrangement cleans the chamber interior and electrodes.

It is still another object of the invention to provide a pH metering apparatus for effluents, as above, in which all mechanical power for the cleansing brush arrangement is derived from the flow of effluent through the chamber.

It is yet another object of the invention to provide a pH metering apparatus for effluents, as above, in which the brush arrangement provides minimal friction to the flow of effluent through the chamber.

It is still a further object of the invention to provide a pH metering apparatus for effluents, as above, in which ports are provided in the chamber for the introduction of fluids to clean the electrodes and standardize the apparatus without dissassembly of the chamber.

It is yet a further object of the invention to provide a pH metering apparatus for effluents, as above, that is lightweight and highly portable, and includes its own portable pumping unit.

These and other objects and advantages of the present invention over existing prior art forms will become more apparent and fully understood from the following description in conjunction with the accompanying drawings.

In general, a self-cleaning apparatus for the monitoring of pH in an effluent process stream includes means for sampling the effluent process stream, housing means for supporting a pH electrode, and means for automatically cleansing the pH electrode entirely powered by the impingement of the fluid process stream upon the means for automatically cleansing. The housing means includes electrode chamber means into which the pH electrode extends. The electrode chamber means receives the effluent process stream sample from the means for sampling and is also automatically, continuously cleansed by the means for automatically cleansing.

BRIEF DESCRIPTION OF THE DRAWINGS

FIG. 1 is a perspective view of a pH monitoring apparatus in accordance with the concept of the present invention.

FIG. 2 is an enlarged, front view of the electrode housing and chamber depicted in FIG. 1.

FIG. 3 is a sectional view taken substantially along the line 3—3 of FIG. 2 showing particularly a portion of the electrode chamber including the electrodes, the cleansing paddlewheel and brush assembly, and the effluent entry and exit ports.

PREFERRED EMBODIMENT FOR CARRYING OUT THE INVENTION

FIG. 1 illustrates an apparatus, generally indicated by the numeral 10, for the monitoring of pH in an effluent treatment system. Apparatus 10 broadly includes effluent sampling assembly 11, a housing 12, electrode assembly 13, electrode chamber 14, and cleansing assembly 15.

Effluent sampling assembly 11 includes a conventional sump pump 16 submerged in effluent process stream 17 for forcing a sample of the same through housing 12 into electrode chamber 14 as detailed hereinbelow. Sump pump 16 is connected to both a suitable power source 20 and ground 21 through conductors 22 as required. Sump pump 16 is mounted atop an inlet base 23 and communicates its discharge through coupling 24 to feed pipe 25.

Additional lengths of a suitable inlet pipe 26, which may be constructed of stainless steel or acrylonitrilebutadine-styrene (ABS) or polyvinyl chloride (PVC) plastic, may be added as necessary or desired to elevate housing 12 to a height above effluent process stream 17 convenient for access. Fittings 27 of either the union or quick release types are interposed between adjoining lengths of inlet pipe 26 to permit ready separation and removal of the housing 12 from the effluent sampling assembly 11, thereby facilitating portability of apparatus 10 and the in-shop repair of housing 12 or its associated elements while an interchanged unit is maintaining operation. A shut-off valve 30 is inserted in inlet pipe 26 in the vicinity of housing 12 to permit isolation of the electrode chamber 14 from effluent process stream 17 without requiring physical detachment from the remaining apparatus 10.

As best seen in FIGS. 2 and 3, situated within housing 12 are electrode chamber 14, inlet port 31, outlet port 32, and a portion of electrode assembly 13 and pH meter 33. Housing 12 may be given any shape sufficient to house these elements, and may itself be formed out of any rigid material impervious to attack by the effluent to be monitored. However, it has been found most preferable to shape housing 12 as a rectangular slab and to manufacture housing 12 out of a transparent thermoplastic such as plexiglass. A transparent housing not only permits visual verification of the proper cleansing action of cleansing assembly 15, but also allows estimation of effluent flow velocity from the rotational speed of cleansing assembly 15.

Electrode chamber 14 includes a cylindrical bore 34 extending only partly through housing 12 and located slightly above the central axis of housing 12, and a removable cap 35 having an O-ring seal 36 and secured to housing 12 by any suitable means such as by bolts 37 screwed into threaded bores 39 in housing 12.

Effluent is received by electrode chamber 14 through a vertical passageway 40 in housing 12 that has one end connected to inlet pipe 26 and whose opposite end tees into inlet port 31, horizontally oriented beneath the horizontal axis of electrode chamber 14. In order to increase the velocity of the sampled effluent process stream entering electrode chamber 14, inlet port 31 is reduced in diameter prior to its entry into electrode chamber 14.

Effluent is discharged from electrode chamber 14 through an outlet port 32 angularly oriented along a radial through the center of electrode chamber 14 and on the side opposite that of inlet port 31. The upper end of a vertical passageway 41 in housing 12 intersects with outlet port 32 and has its lower end connected to a discharge pipe 42 which may be identical to that of inlet pipe 26. As illustrated in FIG. 1, discharge pipe 42 also includes shut-off valve 43 and fittings 44 the same as provided in inlet pipe 26, but unlike that of inlet pipe 26, may be terminated as desired in the effluent process stream 17. Where required discharge pipe 42 may be supported by bracing (not shown) fixed to sump pump 16.

Cleansing assembly 15 includes a paddlewheel 45 and a plurality of cleansing brushes 46. Paddlewheel 45 is rotatable about a shaft 47 cantilevered at one end by cap 35. As best shown in FIG. 2, paddlewheel 45 has a cylindrical wheel core 48 and a plurality of paddles 50 integrally attached at 90° intervals along the circumference of wheel core 48. Paddles 50 include a first arm portion 51 extending at an acute angle from the periphery of wheel core 48 and a second arm portion 52 extending in a direction tangential to the wheel core 48 where joined by the first arm portion 51, resulting in an overall hook-like configuration particularly suited to catch the sampled effluent stream 17 as it enters electrode chamber 14. The volume of effluent that each paddle 50 may trap may be enlarged by forming the inside of each "hook" in the shape of a half-cylinder 53.

Cleansing brushes 46 have their bristles secured inside a slit 54 in each first arm portion 51 of paddles 50. The bristles extend out each half-cylinder 53 into the inside of each "hook" and are slightly longer than the distance to the periphery, resulting in a concave curve being imparted to the bristles and significantly reducing the static coefficient of friction between cleansing assembly 15 and electrode chamber 14.

In the embodiment depicted in FIGS. 1 and 2 a single electrode assembly 13 is employed having both measurement and reference electrodes coaxially situated. Electrode assembly 13 is mounted in housing 12 in any acceptable manner (not relevant herein) so that the ends of the electrodes therein radially protrude into electrode chamber 14 just beyond the periphery thereof.

Operation of apparatus 10 is straightforward. With sump pump 16 immersed within effluent process stream 17, valves 30 and 43 open and the sump pump 16 powered from source 20, a sample of effluent process stream 17 is pumped through feed pipe 25, inlet pipes 26, passageway 40 in housing 12, and inlet port 31 into electrode chamber 14. The incoming effluent process stream has sufficient velocity such that it impinges upon paddlewheel 45, rotating in a counterclockwise direction both paddlewheel 45 and the plurality of cleansing brushes 46 carried thereupon. As brushes 46 rotate within electrode chamber 14, their bristles clean any oily waste or insoluble sediment off the periphery of both electrode chamber 14 and the end of electrode assembly 13 within electrode chamber 14.

The output signals proportional to effluent pH generated by electrode assembly 13 are received by a conventional pH meter 33, which may be mounted within a cutout 49 in housing 12 beneath electrode chamber 14, for well-known processing, display of the numeric value of the pH, and transmission of desired electrical signals to remote electrical data accumulating devices. Alternately, a signal conditioner may be mounted in cutout 49 which would receive the output signals generated by electrode assembly 13 and generate other proportional signals that have been standardized in their signal range.

Two approaches may be taken for calibration of electrode assembly 13. In one approach sump pump 16 is first disconnected from its power source 20, valves 30 and 43 are closed, and plugs removed from their respective threaded access extensions 56, 57 to inlet port 31 and outlet port 32. A cleansing fluid is passed under pressure into electrode chamber 14 via access extension 56 and inlet port 31, flushes electrode chamber 14, and exits via outlet port 32 and access extension 57. In a similar manner a standardized solution is next passed into electrode chamber 14 and the pH electrodes calibrated using existing well-known methods.

In the second approach to calibrating electrode assembly 13, use is made of a quick-disconnect connection 55 for rapid removal of the electrodes from electrode assembly 13, whereupon the electrodes may be momentarily placed in an external standardized solution and apparatus 10 calibrated, followed by return of the electrodes to electrode assembly 13.

In the embodiment depicted herein a single electrode assembly having coaxially aligned measurement and reference electrodes has been utilized. It should be appreciated that not all such commerically available units are designed so as to unobstructedly present the surface of both electrodes to brushes 46. It is equally permissible to employ two independent electrodes so that the active electrode surfaces can be fully exposed to the cleansing action of brushes 46.

It should be understood that because apparatus 10 operates with fluids under slight pressure, it will operate satisfactorily with inlet port 31 and exit port 32 located at any point in the apparatus and with the pH electrodes in any attitudinal orientation above the horizontal. Moreover, it may be desirable to modify the precise configuration of cleansing assembly 15 as a function of the properties of the particular effluent process stream 17 to be monitored.

Inasmuch as the present invention is subject to many variations, modifications and changes in detail, a number of which have been expressly stated herein, it is intended that all matter described throughout this entire specification or shown in the accompanying drawings be interpreted as illustrative and not in a limiting sense. It should thus be evident that a device constructed according to the concept of the present invention, and reasonably equivalent thereto, will accomplish the objects of the present invention and otherwise substantially improve the art of monitoring pH in an effluent process stream with a self-cleaning apparatus.

I claim:

1. A self-cleaning apparatus for the monitoring of pH in an effluent process stream, comprising:
   means for sampling the effluent process stream;
   housing means for supporting a pH electrode, said housing means including electrode chamber means into which said pH electrode extends, said electrode chamber means receiving said effluent process stream sample from said means for sampling; and,
   means for automatically, continuously cleansing said pH electrode and said electrode chamber means, said means for cleansing entirely powered by the impingement of said effluent process stream sample upon said means for cleansing.

2. A self-cleaning apparatus for the monitoring of pH in an effluent process stream, as set forth in claim 1, wherein said means for automatically, continuously cleansing includes paddlewheel means rotatably supported within said electrode chamber means and whose rotation is induced by the impingement thereupon of said effluent process stream.

3. A self-cleaning apparatus for the monitoring of pH in an effluent process stream, as set forth in claim 2, wherein said paddlewheel means carries a plurality of brush means for cleansing the active surface of said pH electrode and the periphery of said electrode chamber as said paddlewheel means rotates within said electrode chamber.

4. A self-cleaning apparatus for the monitoring of pH in an effluent process stream, as set forth in claim 3, wherein said paddlewheel means includes a cylindrical wheel core and a plurality of paddles along the circumference of said cylindrical wheel core, each of said plurality of paddles including a first arm portion extending at an acute angle from the periphery of said cylindrical wheel core, and a second arm portion extending in a direction tangential to said cylindrical wheel core where joined by said first arm portion, said plurality of brush means secured to said first arm portion of said plurality of paddles.

5. A self-cleaning apparatus for the monitoring of pH in an effluent process stream, as set forth in claims 2 or 4, wherein said housing means includes inlet and outlet ports, said inlet port receiving said effluent process stream sample from said means for sampling and increasing the flow velocity thereof for delivery to said electrode chamber, said outlet port receiving the effluent discharge from said electrode chamber.

6. A self-cleaning apparatus for the monitoring of pH in an effluent process stream, as set forth in claim 5, wherein said pH electrode is supported by said housing means utilizing a quick-release type connector.

7. A self-cleaning apparatus for the monitoring of pH in an effluent process stream, as set forth in claim 5, wherein said means for sampling the effluent process stream includes sump pump means for pumping a sample of the effluent process stream to said electrode chamber, the apparatus further including a pH meter mounted in said housing and receiving an output signal from said pH electrode indicative of the pH of the effluent process stream.

8. A self-cleaning apparatus for the monitoring of pH in an effluent process stream, as set forth in claim 5, wherein said housing means further includes access means for introducing cleansing and standardized solutions into said electrode chamber without disassembly of the same and removal of the apparatus from the effluent process stream.

9. A self-cleaning apparatus for the monitoring of pH in an effluent process stream, as set forth in claim 8, wherein said access means are extensions to said inlet port and said outlet port.

* * * * *